United States Patent
Stone et al.

(10) Patent No.: US 8,292,800 B2
(45) Date of Patent: Oct. 23, 2012

(54) IMPLANTABLE PUMP SYSTEM

(75) Inventors: Robert T. Stone, Sunnyvale, CA (US);
Gregory S. Mast, Fremont, CA (US);
Kevin A. Sawyer, Cupertino, CA (US);
Matthew L. Pease, Mountain View, CA (US)

(73) Assignee: Allergan, Inc., Irvine, CA (US)

( * ) Notice: Subject to any disclaimer, the term of this patent is extended or adjusted under 35 U.S.C. 154(b) by 639 days.

(21) Appl. No.: 12/480,911

(22) Filed: Jun. 9, 2009

(65) Prior Publication Data
US 2009/0312785 A1 Dec. 17, 2009

Related U.S. Application Data

(60) Provisional application No. 61/060,578, filed on Jun. 11, 2008.

(51) Int. Cl.
*A61F 2/00* (2006.01)
*A61F 13/00* (2006.01)
*A61M 29/00* (2006.01)

(52) U.S. Cl. .......................... 600/37; 606/191
(58) Field of Classification Search ................ 600/37; 606/191; 417/410.1
See application file for complete search history.

(56) References Cited

U.S. PATENT DOCUMENTS

| | | |
|---|---|---|
| 2,163,048 A | 6/1939 | McKee |
| 3,667,081 A | 6/1972 | Burger |
| 3,840,018 A | 10/1974 | Heifetz |
| 4,118,805 A | 10/1978 | Reimels |
| 4,157,713 A | 6/1979 | Clarey |
| 4,592,339 A | 6/1986 | Kuzmak et al. |
| 4,592,355 A | 6/1986 | Antebi |
| 4,601,713 A | 7/1986 | Fuqua |
| 4,671,351 A | 6/1987 | Rappe |
| 4,696,288 A | 9/1987 | Kuzmak et al. |
| 4,760,837 A | 8/1988 | Petit |
| 4,881,939 A | 11/1989 | Newman |
| 4,883,467 A | 11/1989 | Franetzki et al. |
| 4,944,659 A * | 7/1990 | Labbe et al. ............... 417/413.2 |
| 5,045,060 A | 9/1991 | Melsky et al. |
| 5,074,868 A | 12/1991 | Kuzmak |
| 5,089,019 A | 2/1992 | Grandjean |

(Continued)

FOREIGN PATENT DOCUMENTS

CN 1250382 4/2000

(Continued)

OTHER PUBLICATIONS

Iverson et al., "Recent advances in microscale pumping technologies: a review and evaluation", Microfluids and Nanofluidics, Aug. 1, 2008, Microfluidics and Nanofluidics, vol. 5, Issue 2, pp. 145-174.*

(Continued)

*Primary Examiner* — Charles A Marmor, II
*Assistant Examiner* — Sunita Reddy
(74) *Attorney, Agent, or Firm* — Stephen Donovan; Debra Condino (57) ABSTRACT

A remotely adjustable gastric band system is provided. The system includes a gastric band, an implantable fluid reservoir, and a fluid handling device including a piezoelectric pump, and a drive or controller assembly. The piezoelectric pump includes a diaphragm having a compressible spring positioned at an actuator side of the diaphragm, and a space occupying layer disposed between the compressible spring and the actuator side.

18 Claims, 3 Drawing Sheets

U.S. PATENT DOCUMENTS

| | | | |
|---|---|---|---|
| 5,120,313 A | 6/1992 | Elftman | |
| 5,160,338 A | 11/1992 | Vincent | |
| 5,226,429 A | 7/1993 | Kuzmak | |
| 5,259,399 A | 11/1993 | Brown | |
| 5,326,349 A | 7/1994 | Baraff | |
| 5,360,445 A | 11/1994 | Goldowsky | |
| 5,449,368 A | 9/1995 | Kuzmak | |
| 5,496,312 A | 3/1996 | Klicek | |
| 5,535,752 A | 7/1996 | Halperin et al. | |
| 5,554,113 A | 9/1996 | Novak et al. | |
| 5,562,714 A | 10/1996 | Grevious | |
| 5,601,604 A | 2/1997 | Vincent | |
| 5,658,298 A | 8/1997 | Vincent et al. | |
| 5,676,162 A | 10/1997 | Larson, Jr. et al. | |
| 5,748,200 A | 5/1998 | Funahashi | |
| 5,759,015 A | 6/1998 | Van Lintel et al. | |
| 5,766,232 A | 6/1998 | Grevious et al. | |
| 5,861,014 A | 1/1999 | Familoni | |
| RE36,176 E | 3/1999 | Kuzmak | |
| 5,910,149 A | 6/1999 | Kuzmak | |
| 5,938,669 A | 8/1999 | Klaiber et al. | |
| 6,024,340 A | 2/2000 | Lazarus et al. | |
| 6,024,704 A | 2/2000 | Meador et al. | |
| 6,042,345 A | 3/2000 | Bishop et al. | |
| 6,067,991 A | 5/2000 | Forsell | |
| 6,074,341 A | 6/2000 | Anderson et al. | |
| 6,083,249 A | 7/2000 | Familoni | |
| 6,102,922 A | 8/2000 | Jakobsson et al. | |
| 6,164,933 A * | 12/2000 | Tani et al. | 417/413.2 |
| 6,210,347 B1 | 4/2001 | Forsell | |
| 6,221,024 B1 | 4/2001 | Miesel | |
| 6,306,088 B1 | 10/2001 | Krausman et al. | |
| 6,327,503 B1 | 12/2001 | Familoni | |
| 6,417,750 B1 | 7/2002 | Sohn | |
| 6,432,040 B1 | 8/2002 | Meah | |
| 6,439,539 B1 | 8/2002 | Powell | |
| 6,450,173 B1 | 9/2002 | Forsell | |
| 6,450,946 B1 | 9/2002 | Forsell | |
| 6,453,907 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,454,785 B2 | 9/2002 | De Hoyas Garza | |
| 6,460,543 B1 | 10/2002 | Forsell | |
| 6,461,293 B1 | 10/2002 | Forsell | |
| 6,463,935 B1 | 10/2002 | Forsell | |
| 6,464,628 B1 | 10/2002 | Forsell | |
| 6,470,892 B1 | 10/2002 | Forsell | |
| 6,475,136 B1 | 11/2002 | Forsell | |
| 6,511,490 B2 | 1/2003 | Robert | |
| 6,527,701 B1 | 3/2003 | Sayet et al. | |
| 6,547,801 B1 | 4/2003 | Dargent et al. | |
| 6,579,301 B1 | 6/2003 | Bales et al. | |
| 6,676,674 B1 | 1/2004 | Dudai | |
| 6,681,135 B1 | 1/2004 | Davis et al. | |
| 6,685,668 B1 | 2/2004 | Cho et al. | |
| 6,691,047 B1 | 2/2004 | Fredricks | |
| 6,715,731 B1 | 4/2004 | Post et al. | |
| 6,729,600 B2 | 5/2004 | Mattes et al. | |
| 6,754,527 B2 | 6/2004 | Stroebel et al. | |
| 6,811,136 B2 | 11/2004 | Eberhardt et al. | |
| 6,820,651 B2 | 11/2004 | Seuret et al. | |
| 6,834,201 B2 | 12/2004 | Gillies et al. | |
| 6,871,090 B1 | 3/2005 | He et al. | |
| 6,889,086 B2 | 5/2005 | Mass et al. | |
| 6,940,467 B2 | 9/2005 | Fisher et al. | |
| 6,966,875 B1 | 11/2005 | Longobardi | |
| 7,017,583 B2 | 3/2006 | Forsell | |
| 7,017,883 B2 | 3/2006 | Bayer et al. | |
| 7,021,147 B1 | 4/2006 | Subramanian et al. | |
| 7,037,344 B2 | 5/2006 | Kagan et al. | |
| 7,040,349 B2 | 5/2006 | Moler et al. | |
| 7,048,519 B2 | 5/2006 | Fong et al. | |
| 7,058,434 B2 | 6/2006 | Wang et al. | |
| 7,060,080 B2 | 6/2006 | Bachmann | |
| 7,118,526 B2 | 10/2006 | Egle | |
| 7,128,750 B1 | 10/2006 | Stergiopulos | |
| 7,191,007 B2 | 3/2007 | Desai et al. | |
| 7,198,250 B2 | 4/2007 | East | |
| 7,204,821 B1 | 4/2007 | Clare et al. | |
| 7,206,637 B2 | 4/2007 | Salo | |
| 7,238,191 B2 | 7/2007 | Bachmann | |
| 7,282,023 B2 | 10/2007 | Frering | |
| 7,284,966 B2 | 10/2007 | Xu et al. | |
| 7,288,064 B2 | 10/2007 | Boustani et al. | |
| 7,311,503 B2 | 12/2007 | Van Lintel et al. | |
| 7,311,716 B2 | 12/2007 | Byrum | |
| 7,311,717 B2 | 12/2007 | Egle | |
| 7,314,443 B2 | 1/2008 | Jordan et al. | |
| 7,338,433 B2 | 3/2008 | Coe | |
| 7,351,198 B2 | 4/2008 | Byrum et al. | |
| 7,351,240 B2 | 4/2008 | Hassler, Jr. et al. | |
| 7,353,747 B2 | 4/2008 | Swayze et al. | |
| 7,364,542 B2 | 4/2008 | Jambor et al. | |
| 7,366,571 B2 | 4/2008 | Armstrong | |
| 7,367,340 B2 | 5/2008 | Nelson et al. | |
| 7,367,937 B2 | 5/2008 | Jambor et al. | |
| 7,374,565 B2 | 5/2008 | Hassler, Jr. et al. | |
| 7,390,294 B2 | 6/2008 | Hassler, Jr. | |
| 7,396,353 B2 | 7/2008 | Lorenzen et al. | |
| 7,416,528 B2 | 8/2008 | Crawford et al. | |
| 7,481,763 B2 | 1/2009 | Hassler et al. | |
| 7,500,944 B2 | 3/2009 | Byrum et al. | |
| 7,530,943 B2 | 5/2009 | Lechner | |
| 7,594,885 B2 | 9/2009 | Byrum | |
| 7,599,743 B2 | 10/2009 | Hassler, Jr. et al. | |
| 7,599,744 B2 | 10/2009 | Giordano et al. | |
| 7,601,162 B2 | 10/2009 | Hassler, Jr. et al. | |
| 7,615,001 B2 | 11/2009 | Jambor et al. | |
| 7,618,365 B2 | 11/2009 | Jambor et al. | |
| 7,658,196 B2 | 2/2010 | Ferreri et al. | |
| 7,699,770 B2 | 4/2010 | Hassler, Jr. et al. | |
| 7,727,141 B2 | 6/2010 | Hassler, Jr. et al. | |
| 7,758,493 B2 | 7/2010 | Gingras | |
| 7,766,815 B2 | 8/2010 | Ortiz | |
| 7,771,439 B2 | 8/2010 | Griffiths | |
| 7,775,215 B2 | 8/2010 | Hassler, Jr. et al. | |
| 7,775,966 B2 | 8/2010 | Dlugos et al. | |
| 7,794,386 B2 | 9/2010 | Brooks | |
| 7,811,298 B2 | 10/2010 | Birk | |
| 7,844,342 B2 | 11/2010 | Dlugos et al. | |
| 2001/0011543 A1 | 8/2001 | Forsell | |
| 2002/0072780 A1 | 6/2002 | Foley | |
| 2002/0091395 A1 | 7/2002 | Gabbay | |
| 2002/0095181 A1 | 7/2002 | Beyar | |
| 2002/0139208 A1 | 10/2002 | Yatskov | |
| 2002/0198548 A1 | 12/2002 | Robert | |
| 2003/0019498 A1 | 1/2003 | Forsell | |
| 2003/0045775 A1 | 3/2003 | Forsell | |
| 2003/0055311 A1 * | 3/2003 | Neukermans et al. | 600/25 |
| 2003/0066536 A1 | 4/2003 | Forsell | |
| 2003/0073880 A1 | 4/2003 | Polsky et al. | |
| 2003/0158569 A1 | 8/2003 | Wazne | |
| 2003/0208212 A1 | 11/2003 | Cigaina | |
| 2004/0000843 A1 * | 1/2004 | East | 310/331 |
| 2004/0044332 A1 | 3/2004 | Stergiopulos | |
| 2004/0059393 A1 | 3/2004 | Policker et al. | |
| 2004/0133219 A1 | 7/2004 | Forsell | |
| 2004/0147816 A1 | 7/2004 | Policker et al. | |
| 2004/0148034 A1 | 7/2004 | Kagan et al. | |
| 2004/0153106 A1 | 8/2004 | Dudai | |
| 2004/0162595 A1 | 8/2004 | Foley | |
| 2004/0215159 A1 | 10/2004 | Forsell | |
| 2004/0230137 A1 | 11/2004 | Mouton | |
| 2004/0254536 A1 | 12/2004 | Conlon et al. | |
| 2004/0254537 A1 | 12/2004 | Conlon et al. | |
| 2004/0260319 A1 | 12/2004 | Egle | |
| 2004/0267288 A1 | 12/2004 | Byrum et al. | |
| 2004/0267291 A1 | 12/2004 | Byrum et al. | |
| 2004/0267292 A1 | 12/2004 | Byrum et al. | |
| 2004/0267293 A1 | 12/2004 | Byrum et al. | |
| 2004/0267377 A1 | 12/2004 | Egle | |
| 2005/0002984 A1 | 1/2005 | Byrum et al. | |
| 2005/0038484 A1 | 2/2005 | Knudson et al. | |
| 2005/0055039 A1 | 3/2005 | Burnett et al. | |
| 2005/0070934 A1 | 3/2005 | Tanaka et al. | |
| 2005/0070937 A1 | 3/2005 | Jambor et al. | |

| | | | | | | |
|---|---|---|---|---|---|---|
| 2005/0104457 A1 | 5/2005 | Jordan et al. | | 2008/0287976 A1 | 11/2008 | Weaner et al. |
| 2005/0119672 A1 | 6/2005 | Benchetrit | | 2008/0319435 A1 | 12/2008 | Rioux et al. |
| 2005/0119674 A1 | 6/2005 | Gingras | | 2009/0054914 A1 | 2/2009 | Lechner |
| 2005/0131383 A1 | 6/2005 | Chen et al. | | 2009/0062825 A1 | 3/2009 | Pool et al. |
| 2005/0131485 A1 | 6/2005 | Knudson et al. | | 2009/0062826 A1 | 3/2009 | Steffen |
| 2005/0143765 A1 | 6/2005 | Bachmann et al. | | 2009/0082793 A1 | 3/2009 | Birk |
| 2005/0143766 A1 | 6/2005 | Bachmann et al. | | 2009/0118572 A1 | 5/2009 | Lechner |
| 2005/0183730 A1 | 8/2005 | Byrum | | 2009/0157106 A1 | 6/2009 | Marcotte et al. |
| 2005/0192531 A1 | 9/2005 | Birk | | 2009/0157107 A1 | 6/2009 | Kierath et al. |
| 2005/0192601 A1 | 9/2005 | Demarais | | 2009/0157113 A1 | 6/2009 | Marcotte et al. |
| 2005/0216042 A1 | 9/2005 | Gertner | | 2009/0171375 A1 | 7/2009 | Coe et al. |
| 2005/0228415 A1 | 10/2005 | Gertner | | 2009/0171378 A1 | 7/2009 | Coe et al. |
| 2005/0240155 A1 | 10/2005 | Conlon | | 2009/0171379 A1 | 7/2009 | Coe et al. |
| 2005/0240156 A1 | 10/2005 | Conlon | | 2009/0192404 A1 | 7/2009 | Ortiz et al. |
| 2005/0240279 A1 | 10/2005 | Kagan et al. | | 2009/0192415 A1 | 7/2009 | Ortiz et al. |
| 2005/0244288 A1 | 11/2005 | O'Neill | | 2009/0192533 A1 | 7/2009 | Dlugos, Jr. et al. |
| 2005/0250979 A1 | 11/2005 | Coe | | 2009/0192534 A1 | 7/2009 | Ortiz et al. |
| 2005/0251181 A1 | 11/2005 | Bachmann | | 2009/0192541 A1 | 7/2009 | Ortiz et al. |
| 2005/0251182 A1 | 11/2005 | Bachmann | | 2009/0198261 A1 | 8/2009 | Schweikert |
| 2005/0267406 A1* | 12/2005 | Hassler .................. 604/96.01 | | 2009/0202387 A1 | 8/2009 | Dlugos, Jr. et al. |
| 2005/0267500 A1* | 12/2005 | Hassler et al. ............. 606/157 | | 2009/0204131 A1 | 8/2009 | Ortiz et al. |
| 2005/0267533 A1 | 12/2005 | Gertner | | 2009/0204132 A1 | 8/2009 | Ortiz et al. |
| 2005/0277899 A1 | 12/2005 | Conlon et al. | | 2009/0204141 A1 | 8/2009 | Dlugos, Jr. et al. |
| 2005/0283041 A1 | 12/2005 | Egle | | 2009/0204179 A1 | 8/2009 | Dlugos, Jr. et al. |
| 2005/0288739 A1 | 12/2005 | Hassler | | 2009/0209995 A1 | 8/2009 | Byrum et al. |
| 2005/0288740 A1 | 12/2005 | Hassler | | 2009/0216255 A1 | 8/2009 | Coe et al. |
| 2006/0041183 A1 | 2/2006 | Massen et al. | | 2009/0222031 A1 | 9/2009 | Axelsson |
| 2006/0074439 A1 | 4/2006 | Garner et al. | | 2009/0222065 A1 | 9/2009 | Dlugos, Jr. et al. |
| 2006/0074473 A1 | 4/2006 | Gertner | | 2009/0228072 A1 | 9/2009 | Coe et al. |
| 2006/0089571 A1 | 4/2006 | Gertner | | 2009/0270904 A1 | 10/2009 | Birk et al. |
| 2006/0142700 A1 | 6/2006 | Birk | | 2009/0306462 A1 | 12/2009 | Lechner |
| 2006/0161186 A1 | 7/2006 | Hassler, Jr. et al. | | 2009/0312785 A1 | 12/2009 | Stone et al. |
| 2006/0173238 A1 | 8/2006 | Starkelbaum | | 2010/0010291 A1 | 1/2010 | Birk et al. |
| 2006/0173424 A1 | 8/2006 | Conlon | | 2010/0087843 A1 | 4/2010 | Bertolote et al. |
| 2006/0178555 A1 | 8/2006 | Bortolotti | | 2010/0099945 A1 | 4/2010 | Birk et al. |
| 2006/0183967 A1 | 8/2006 | Lechner | | 2010/0100079 A1 | 4/2010 | Berkcan |
| 2006/0189887 A1 | 8/2006 | Hassler et al. | | 2010/0152532 A1 | 6/2010 | Marcotte |
| 2006/0189888 A1 | 8/2006 | Hassler, Jr. et al. | | 2010/0185049 A1 | 7/2010 | Birk et al. |
| 2006/0189889 A1 | 8/2006 | Gertner | | 2010/0191271 A1 | 7/2010 | Lau et al. |
| 2006/0195139 A1 | 8/2006 | Gertner | | 2010/0228080 A1 | 9/2010 | Tavori et al. |
| 2006/0197412 A1 | 9/2006 | Rasmussen | | 2010/0249803 A1 | 9/2010 | Griffiths |
| 2006/0199997 A1 | 9/2006 | Hassler et al. | | 2010/0280310 A1 | 11/2010 | Raven |
| 2006/0211912 A1 | 9/2006 | Dlugos et al. | | 2010/0305397 A1 | 12/2010 | Birk et al. |
| 2006/0211913 A1 | 9/2006 | Dlugos et al. | | 2010/0324358 A1 | 12/2010 | Birk et al. |
| 2006/0211914 A1 | 9/2006 | Hassler, Jr. et al. | | 2010/0324359 A1 | 12/2010 | Birk |
| 2006/0212053 A1 | 9/2006 | Gertner | | | | |
| 2006/2345448 | 10/2006 | Roslin et al. | | FOREIGN PATENT DOCUMENTS | | |
| 2006/0252982 A1* | 11/2006 | Hassler et al. .............. 600/37 | | CN | 1367670 | 9/2002 |
| 2007/0027356 A1 | 2/2007 | Ortiz | | DE | 4225524 | 2/1994 |
| 2007/0078476 A1 | 4/2007 | Hull et al. | | DE | 10020688 | 12/2000 |
| 2007/0125826 A1 | 6/2007 | Shelton | | EP | 0119596 | 9/1984 |
| 2007/0156013 A1* | 7/2007 | Birk .................. 600/37 | | EP | 0230747 | 8/1987 |
| 2007/0167672 A1 | 7/2007 | Dlugos et al. | | EP | 0611561 | 8/1994 |
| 2007/0185462 A1 | 8/2007 | Byrum | | EP | 0695558 | 2/1996 |
| 2007/0218083 A1 | 9/2007 | Brooks | | EP | 0867808 | 11/1998 |
| 2007/0232848 A1 | 10/2007 | Forsell | | EP | 1072282 | 1/2001 |
| 2007/0235083 A1 | 10/2007 | Dlugos | | EP | 1396242 | 3/2004 |
| 2007/0250085 A1 | 10/2007 | Bachmann et al. | | EP | 1396243 | 3/2004 |
| 2007/0250086 A1 | 10/2007 | Wiley et al. | | EP | 1491167 | 12/2004 |
| 2007/0255336 A1 | 11/2007 | Herbert et al. | | EP | 1547549 | 6/2005 |
| 2007/0265598 A1 | 11/2007 | Karasik | | EP | 1600183 | 11/2005 |
| 2007/0265645 A1 | 11/2007 | Birk et al. | | EP | 1602346 | 12/2005 |
| 2008/0009680 A1 | 1/2008 | Hassler, Jr. | | EP | 1704833 | 9/2006 |
| 2008/0015406 A1 | 1/2008 | Dlugos et al. | | EP | 1754890 A2 | 11/2006 |
| 2008/0027469 A1 | 1/2008 | Bachmann | | EP | 1736123 | 12/2006 |
| 2008/0097496 A1 | 4/2008 | Chang et al. | | EP | 1719480 A2 | 2/2007 |
| 2008/0108862 A1 | 5/2008 | Jordan et al. | | EP | 2074970 | 7/2009 |
| 2008/0166028 A1* | 7/2008 | Turek et al. .................... 382/124 | | EP | 2074971 | 7/2009 |
| 2008/0221598 A1 | 9/2008 | Dlugos et al. | | EP | 2087862 | 8/2009 |
| 2008/0249806 A1 | 10/2008 | Dlugos et al. | | EP | 2095796 | 9/2009 |
| 2008/0250340 A1 | 10/2008 | Dlugos et al. | | EP | 2095798 | 9/2009 |
| 2008/0250341 A1 | 10/2008 | Dlugos et al. | | FR | 2797181 | 2/2001 |
| 2008/0255403 A1 | 10/2008 | Voegele et al. | | FR | 2823663 | 10/2002 |
| 2008/0255414 A1 | 10/2008 | Voegele et al. | | FR | 2855744 | 12/2004 |
| 2008/0255425 A1 | 10/2008 | Voegele et al. | | FR | 2921822 | 4/2009 |
| 2008/0255459 A1 | 10/2008 | Voegele et al. | | WO | WO 1989/11701 | 11/1989 |
| 2008/0255537 A1 | 10/2008 | Voegele et al. | | WO | WO 00/09047 | 2/2000 |
| 2008/0287969 A1 | 11/2008 | Tsonton et al. | | WO | WO 00/09048 | 2/2000 |
| 2008/0287974 A1 | 11/2008 | Widenhouse et al. | | WO | WO 00/15158 | 3/2000 |

| | | |
|---|---|---|
| WO | WO 00/66196 | 11/2000 |
| WO | WO 01/10359 | 2/2001 |
| WO | WO 01/12078 | 2/2001 |
| WO | WO 01/47575 | 7/2001 |
| WO | WO 01/49245 | 7/2001 |
| WO | WO 01/70131 A1 | 9/2001 |
| WO | WO 02/26317 | 4/2002 |
| WO | WO 02/053093 | 7/2002 |
| WO | WO 02/065948 | 8/2002 |
| WO | WO 03/077191 | 9/2003 |
| WO | WO 03/105732 | 12/2003 |
| WO | WO 2004/014245 | 2/2004 |
| WO | WO 2004/019671 | 3/2004 |
| WO | WO 2005/007232 | 1/2005 |
| WO | WO 2005/009305 | 2/2005 |
| WO | WO 2005/087147 | 9/2005 |
| WO | WO 2005/094447 | 10/2005 |
| WO | WO 2006/083885 | 8/2006 |
| WO | WO 2006/108203 | 10/2006 |
| WO | WO 2008/109300 | 9/2008 |
| WO | WO 2009/132127 | 10/2009 |

OTHER PUBLICATIONS

Corno et al.; "A new implantable device for telemetric control of pulmonary blood flow," New Ideas; accepted Jul. 22, 2002.

Corno et al.; "FloWatchTM in clipped and inclipped position," Interact Cardio Vasc Thorac Surg 2002; 1:46-49.

BioEnterics Lap-Band Adjustable Gastric Banding System, Inamed Health, pub. Aug. 28, 2003 pp. 1-115.

\* cited by examiner

IMPLANTABLE PUMP SYSTEM

RELATED APPLICATION

This application claims the benefit of U.S. Provisional Patent Application No. 61/060,578, filed on Jun. 11, 2008, the entire disclosure of which is incorporated herein in by this specific reference.

BACKGROUND

The present invention generally relates to implantable pumps for medical uses and more specifically relates to an implantable piezoelectric pump for a remotely adjustable gastric banding system.

Adjustable gastric banding is a medical procedure which can provide a safer, more effective, and substantially less invasive alternative to conventional gastric bypass surgery for the treatment of obesity. It has been recognized that sustained weight loss can be achieved through a laparoscopically-placed gastric band, for example, the LAP-BAND® gastric band or the LAP BAND AP® gastric band.

Generally, the LAP-BAND® gastric band is placed about an upper portion of a patient's stomach to form a smaller upper stomach "pouch" and a stoma that restricts the passage of food into a larger lower portion of the stomach. When the stoma is of an appropriate size, food held in the upper stomach pouch provides a feeling of satiety or fullness that discourages overeating.

One highly desirable aspect of gastric banding procedures is that gastric banding procedures are generally performed laparoscopically, and are considered to be minimally invasive procedures, relative to more invasive "open" surgical procedures such as gastric bypass surgery. Consequently, gastric banding procedures may cause less discomfort to the patient and generally require a shorter recovery time.

In addition, gastric banding procedures are substantially entirely reversible. If a doctor and patient decide to remove the gastric band after placement, for example, in the event that the desired weight loss is not being achieved and/or the patient cannot adjust to new eating habits required as a gastric banding patient, the removal of the gastric band will likely restore the stomach to the original size and form. Unlike gastric bypass procedures, gastric banding procedures require no permanent surgical modification to the gastrointestinal tract.

It has been recognized that over time, the stoma created by the gastric band on the stomach may need adjustment in order to maintain an appropriate size. To ensure a desired weight-loss result and comfort to the patient, the stoma should be neither too restrictive nor too loose. Accordingly, hydraulically adjustable gastric bands, for example the LAP BAND AP® system, include an inflatable portion of the band which can be used to adjust the size of the stoma. The inflatable portion can be "inflated" or filled with saline to an increased volume, and "deflated" or drained to a decreased volume, to achieve the ideal stoma size. Filling and draining is accomplished through a fluid access port positioned subcutaneously in the patient. In other words, by adding or removing fluid to or from the inflatable portion, e.g. by means of a hypodermic needle inserted into the access port, a physician can adjust the size of an inner circumference of the band about the stomach.

Automatically adjustable hydraulic gastric banding systems, as well as remotely adjustable hydraulic gastric banding systems, have been proposed.

Birk, U.S. Patent Application Publication No. 2007/0156013, commonly assigned herewith and incorporated in its entirety herein by this specific reference, discloses an automatically adjustable gastric banding system including an adjustment assembly that includes a sensor for sensing fluid pressure in the inflatable portion of a gastric band. The adjustment assembly further includes an implantable pump connected to the expandable portion, and a controller for activating the pump to adjust volume of fluid in the inflatable portion of the band based on a sensed fluid pressure.

Birk et al. U.S. Patent Application Publication No. 2007/0265645, commonly assigned herewith and incorporated in its entirety herein by this specific reference, discloses a self-regulating gastric band adjustment assembly including an implantable fluid reservoir for containing a volume of the fluid useful for adjusting a gastric band.

Coe, U.S. Pat. No. 7,338,433, commonly assigned herewith and incorporated in its entirety herein by this specific reference, discloses a remotely controllable gastric banding system. The system includes a pressurized fluid reservoir coupled to an inflatable portion of a gastric band. Valves are provided for controlling fluid flow between the pressurized reservoir and the inflatable portion of the band. A controller is used to control the valves, thereby regulating the volume change in the inflatable portion of the band. The controller is remotely controllable from outside of the patient.

There has yet to be proposed a piezoelectrically driven pump which is straightforward in construction, and acceptably reliable and useful in an implanted environment particularly for use in the adjustment of gastric bands. The operability of a piezoelectric pump is highly dependent upon the environment in which it is operated. For example, piezoelectric materials such as ceramics are extremely fragile and highly sensitive. Ideally, a piezoelectric material used as an actuator for a pump must be kept in a moisture-free, non-condensing environment in order to remain reliable and operable. Polymers which are known to be biocompatible are not ideal materials as pump components because these materials tend to allow diffusion of water vapor. Further, as a result of even small changes in temperature and the relatively sealed nature of a pump implanted in a living body, liquid will tend to condense and accumulate in any pump space or void that is not absolutely hermetic.

While the various implantable pump systems which have been proposed appear to at least recognize the need for accurate and reliable technologies for maintaining a stoma size in a gastric banding patient, there still remains a need for more sophisticated implantable pump systems for use with remotely adjustable gastric bands. The present invention has been developed to provide an accurate, reliable, safe and highly sophisticated implantable piezoelectric pump system for medical uses, for example, for use in adjustable gastric banding systems.

SUMMARY OF THE INVENTION

Accordingly, in one broad aspect of the invention, a system for facilitating obesity control is provided. In a more specific aspect of the invention, the present invention provides an implantable fluid handling device including a piezoelectric pump for facilitating remote and/or automatic adjustment of a stoma size in a gastric banding patient.

In an exemplary embodiment of the invention, the implantable fluid handling device generally includes a high precision, piezoelectric pump assembly couplable between an implantable fluid reservoir and an inflatable portion of a gastric band. When in use, the implantable fluid reservoir and inflatable portion of the gastric band make up components of a closed loop fluid system similar to previously proposed remotely and/or automatically hydraulically adjustable gastric banding systems mentioned elsewhere herein.

In accordance with the present invention, the piezoelectric pump assembly includes a flexible or bendable, piezoelectrically activatable component which functions as a pump diaphragm. The diaphragm generally includes a working side and an actuator side.

For example, the pump assembly further comprises a housing or body in which the diaphragm is located. The body at least partially defines a pump chamber on the working side of the diaphragm. The working side of the diaphragm may define a surface or boundary of the pump chamber. The pump chamber contains the fluid being pumped, for example, saline or other biocompatible liquid. The pump chamber includes an inlet port couplable to the implantable fluid reservoir, and an outlet port couplable to the inflatable portion of the gastric band.

On the actuator side of the diaphragm is an actuating region of the body. The actuating region is structured to accommodate for the flexing or bending of the diaphragm. Within the actuating region are one or more piezoelectric elements such as a ceramic element. The piezoelectric elements may be located on or may be a component of the actuating side of the diaphragm. These piezoelectric elements are typically quite fragile and electrically sensitive and are therefore sealed apart from the pump chamber containing the saline or other biocompatible fluid.

Upon application of an electrical charge to the piezoelectric element, the diaphragm is caused to bend or flex. Such bending or flexing alters the volume of the pump chamber, thereby pumping fluid into the inflatable portion of the band.

In addition, the implantable fluid handling device may further comprise a controller or drive assembly effective to actuate the piezoelectric diaphragm to cause metered movement of fluid into and out from of the pump chamber.

In an especially advantageous aspect of the invention, the fluid handling device is designed to maintain operating integrity of the piezoelectric actuation in order to ensure reliable long term use of the system in the body of the patient.

For example, in one embodiment, a space occupying element is provided and is structured to maintain operating integrity of piezoelectric diaphragm assembly. For example, the space occupying element may comprise a non-conductive material which overlies, covers or seals the actuator side of the diaphragm. Preferably, the space occupying element is substantially entirely hermetically sealed to the actuator side of the diaphragm so as to substantially entirely seal the piezoelectric components from any contact with liquid water, saline, body fluid or condensation which might otherwise occur without the space occupying element in place.

In one embodiment, the space occupying layer comprises a hydrophobic liquid, for example, silicone oil, or other suitable non-conductive material.

In another aspect of the invention, the fluid handling device further comprises a compressible element, for example, a gas filled, sealed void located in the actuating region. In a specific embodiment, the compressible element comprises a compressible spring assembly. The compressible spring assembly comprises a first portion distal to the actuator side of the diaphragm, and a substantially opposing second portion distal to the first portion. A sealed void, for example, a gas-filled void, is defined between the first portion and the second portion. The first portion may comprise a relatively thin, flexible plate, foil or membrane. The second portion is relatively more rigid than the first portion. In an exemplary embodiment, the first portion of the compressible spring assembly comprises a flexible metallic membrane and the second portion of the compressible spring assembly comprises a rigid plate made of the same material as the metallic membrane. In one embodiment, each of the first portion and the second portion of the compressible spring assembly comprises titanium. For example, the first portion may comprise a flexible titanium foil and the second portion may comprise a relatively rigid titanium plate. Preferably, the void space is hermetically sealed between the first and second portions of the compressible spring assembly. In some embodiments, the first portion and second portion formed as a unitary structure.

In a specific exemplary embodiment, the fluid handling device comprises both a space occupying layer, for example, a layer of silicone oil, and a compressible spring assembly, for example, a hermetically sealed gas spring disk. The layer of silicone oil is sealed between the actuator side of the piezoelectric diaphragm assembly and a flexible surface of the compressible spring assembly.

Each and every feature described herein, and each and every combination of two or more of such features, is included within the scope of the present invention provided that the features included in such a combination are not mutually inconsistent.

BRIEF DESCRIPTION OF THE DRAWINGS

The present invention will be more clearly understood and the aspects and advantages thereof may be better appreciated with reference to the following detailed description when considered in conjunction with the accompanying drawings of which.

DETAILED DESCRIPTION

Figure 1:
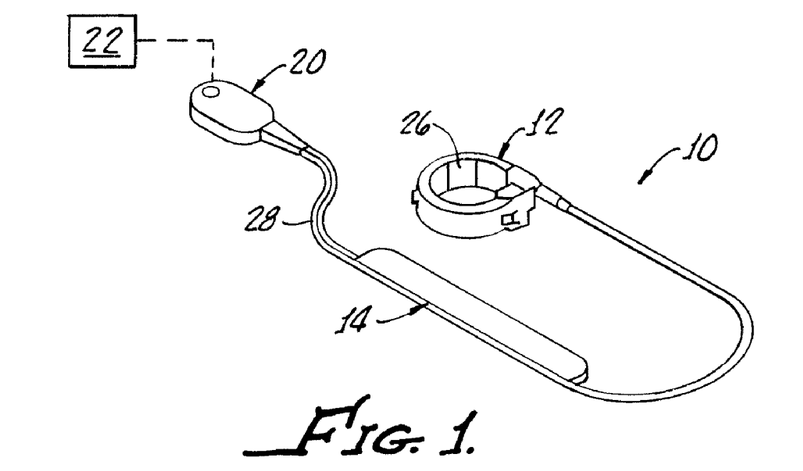
FIG. 1 is a perspective view of a system for controlling or treating obesity in accordance with one aspect of the invention, the system generally comprising an adjustable gastric band, an implantable fluid reservoir, an implantable high precision fluid handling device and a driver or controller for remotely operating or actuating the fluid handling device.
Figure 2:
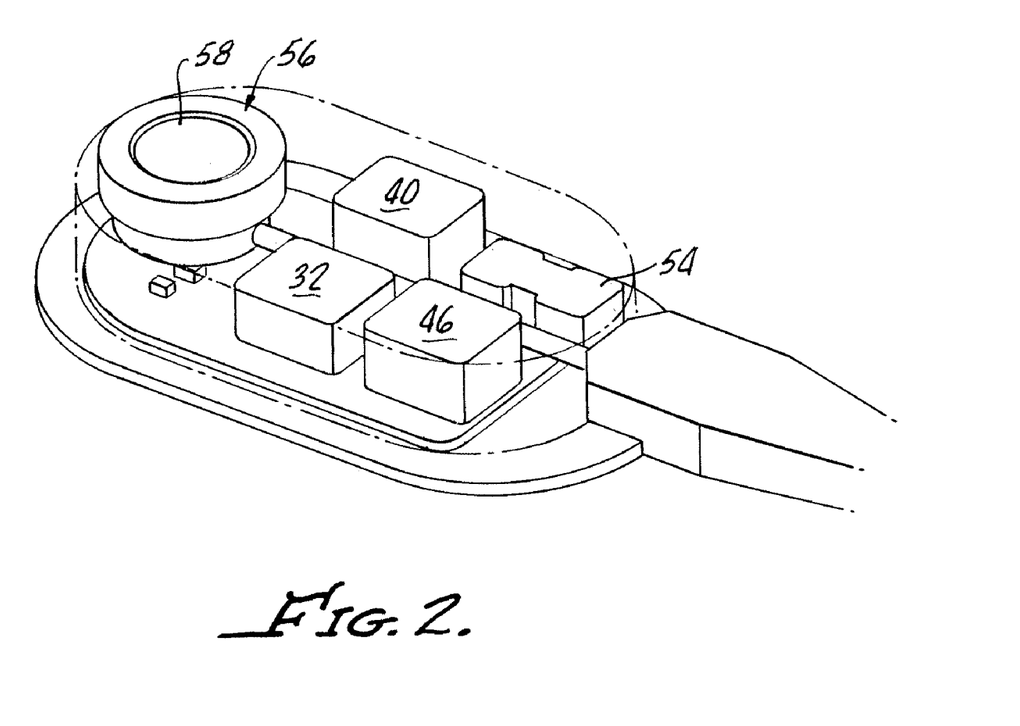
FIG. 2 is a somewhat simplified cutaway view of the implantable fluid handling device shown in FIG. 1, in accordance with an embodiment of the invention.

Turning now to FIG. 1, in a specific embodiment of the invention, a system for controlling obesity or facilitating weight loss is generally shown at 10. The system 10 generally includes a gastric band 12, for example, a LAP-BAND AP® gastric band available from Allergan, Inc., a fluid reservoir 14, for example a saline reservoir, a fluid handling device 20 including a piezoelectric pump assembly, and a drive or controller assembly 22 effective to control or actuate the fluid handling device 20. Along with the controller assembly 22, the fluid handling device 20 may be used to replace or compliment a conventional access port and syringe in a conventional laparoscopic gastric banding system (not shown).

The surgical technique to place the present system 10 may be somewhat similar to the placement of known laparoscopic gastric banding systems. For example, the gastric band 12 is placed around an upper portion of the stomach (not shown) to form the stoma and stomach "pouch". The fluid handling device 20 is sutured or otherwise secured to the rectus muscle sheath. For this purpose, the fluid handling device 20 may include suture apertures or other suitable structure to facilitate securing the device 20 in place. A fluid line 28, for example, tubing, from the fluid handling device 20 is passed through the rectus muscle into the peritoneal cavity where it is coupled to the gastric band 12.

Regarding the general flow path of fluid in the present system 10, the fluid handling device 20 is positioned (in a fluid flow sense) between the fluid reservoir 14 and the inflatable portion 26 of the gastric band 12. The fluid reservoir 14 may be a soft, collapsible member coupled to the fluid handling assembly 20 and in communication with line 28. Alternatively, the fluid reservoir 14 may simply be a portion, for example, an expandable portion, of the fluid line 28.

The fluid handling device 20 is designed to be capable of moving precisely metered volumes of liquid, for example, saline, into and out of the inflatable portion 26 of the gastric band 12.

Figure 3:
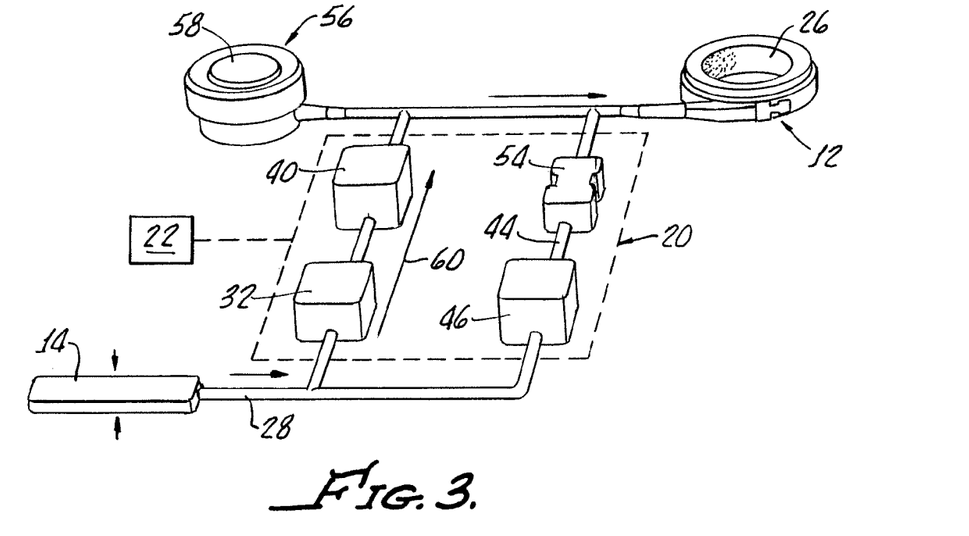
FIG. 3 is flow diagram showing fluid flow in the implantable fluid handling device during filling or tightening of the adjustable gastric band.
Figure 4:
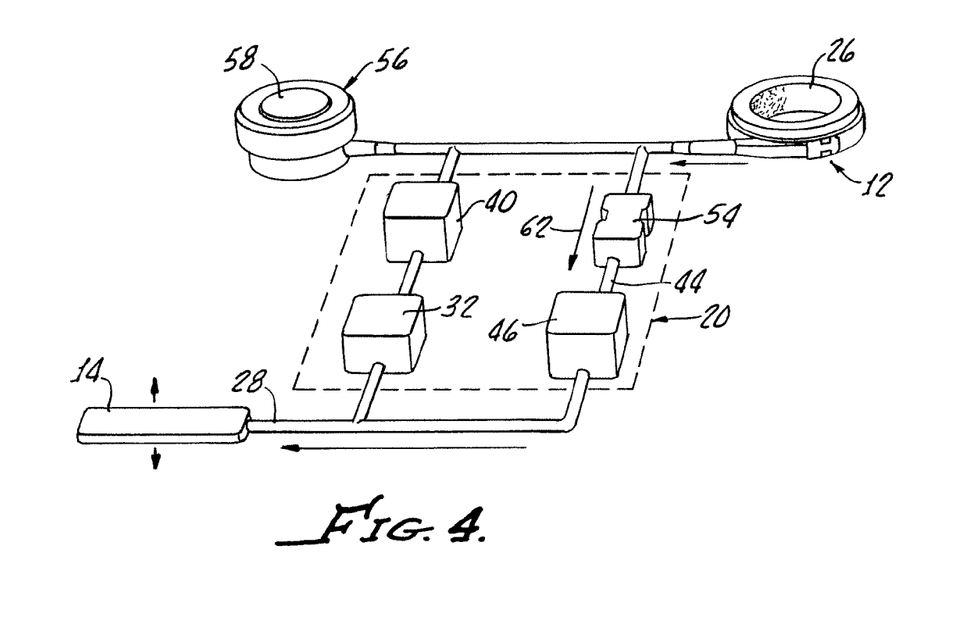
FIG. 4 is flow diagram showing fluid flow in the implantable fluid handling device during draining or loosening of the adjustable gastric band.

A flow diagram of an exemplary fluid handling device 20 is shown schematically in FIGS. 3 and 4. As shown, the inflatable portion 26 of the gastric band 12, the fluid handling device 20, and the fluid reservoir 14 comprise a "closed" fluid system. The fluid handling device 20 is effective to pump small, metered volumes of fluid into the inflatable member 26. The fluid handling device 20 achieves a metered volume transfer in part by means of a high precision unidirectional piezoelectric pump 32. In the presently shown embodiment, the pump 32 is unidirectional in that it allows flow only in a direction from the fluid reservoir 14 to the inflatable portion 26. Check valve 40 prevents backflow into the pump 32. The fluid handling device 20 further includes a parallel flow line 44 including valve 46 for allowing fluid flow, or draining of fluid in a direction from the inflatable member 26 to the fluid reservoir 14.

In the exemplary embodiment shown, the fluid handling device 20 further includes a sensor element 54, for example, a pressure sensor and/or flow sensor effective to sense pressure and/or flow of fluid in the line. Signals from sensor element 54 may be processed in the controller assembly 22. Pump 32 and valves 40 and 46 are remotely activatable by means of controller assembly 22, the activation being based at least in part on the sensed signals. Further disclosure which may be useful for a better understanding of the remote and/or automatically adjustable aspects of the present gastric banding systems may be found in Birk, U.S. Patent Application Publication No. 2007/0156013; Birk et al. U.S. Patent Application Publication No. 2007/0265645; and Coe, U.S. Pat. No. 7,338,433.

As shown, the fluid handling device 20 further includes an override access port 56 for enabling manual or conventional adjustment of the inflatable member 26, for example, by enabling addition or removal of fluid from the inflatable portion 26 by means of a syringe inserted into septum 58.

Preferably, during the time periods between filling/draining adjustments of the gastric band 12, each of valve 40 and valve 46 is closed to fluid flow. In FIG. 3, the flow diagram shows direction of fluid flow during band inflation or expansion. Just before pumping is initiated, valve 40 in line with pump 32 is opened. Activation of pump 32 draws fluid out of the fluid reservoir 14 and in the direction of arrow 60. Once the proper amount of fluid has been transferred to the inflatable portion 26 of the gastric band 12, (for example as sensed by sensor 54) the controller assembly 22 shuts off the pump 32 and closes the valve 40.

In FIG. 4, the flow diagram shows the direction of fluid flow during band deflation or draining. In order to loosen the band, controller assembly 22 is operated to open valve 46, causing fluid to drain from the inflatable portion 26 of the gastric band 12 in a direction represented by arrow 62. When fluid pressure in the gastric band 12 is as desired, for example, as sensed by sensor 54, valve 46 is closed.

The present invention advantageously further provides a highly effective and reliable pump structure which will now be described. As mentioned elsewhere herein, the pump 32 of fluid handling device 20 preferably is a piezoelectrically activatable, unidirectional micropump, such as shown generally in cross-sectional view in FIGS. 5 and 6 and described hereinafter. It is to be appreciated that the piezoelectric pump device 32 is considered to be, in itself and particularly when used in an implanted environment, an embodiment of the present invention.

Figure 5:
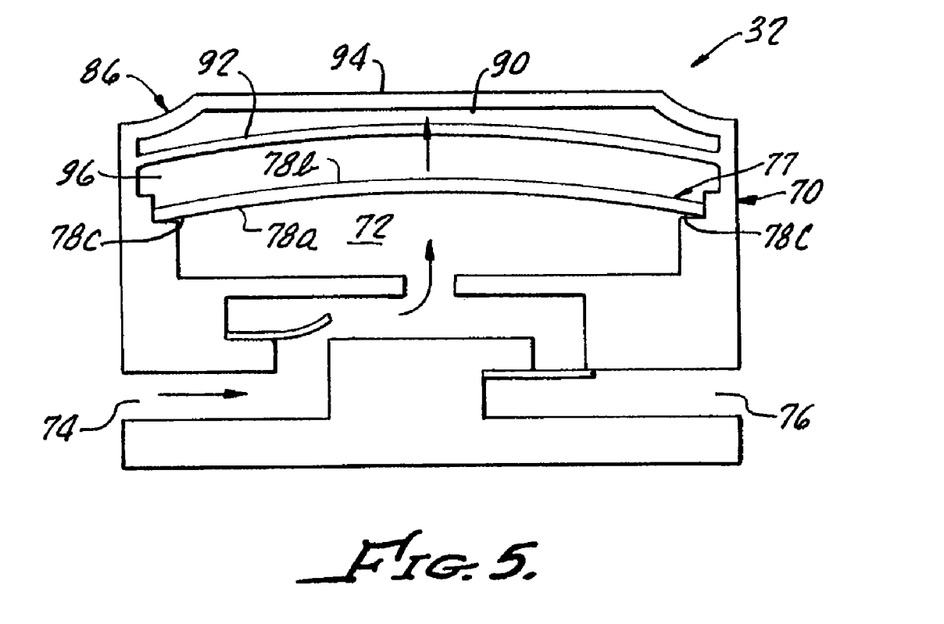
FIG. 5 is simplified cross-sectional view of a piezoelectric pump in accordance with an embodiment of the invention, the pump being shown during drawing of fluid into a pump reservoir thereof.
Figure 6:
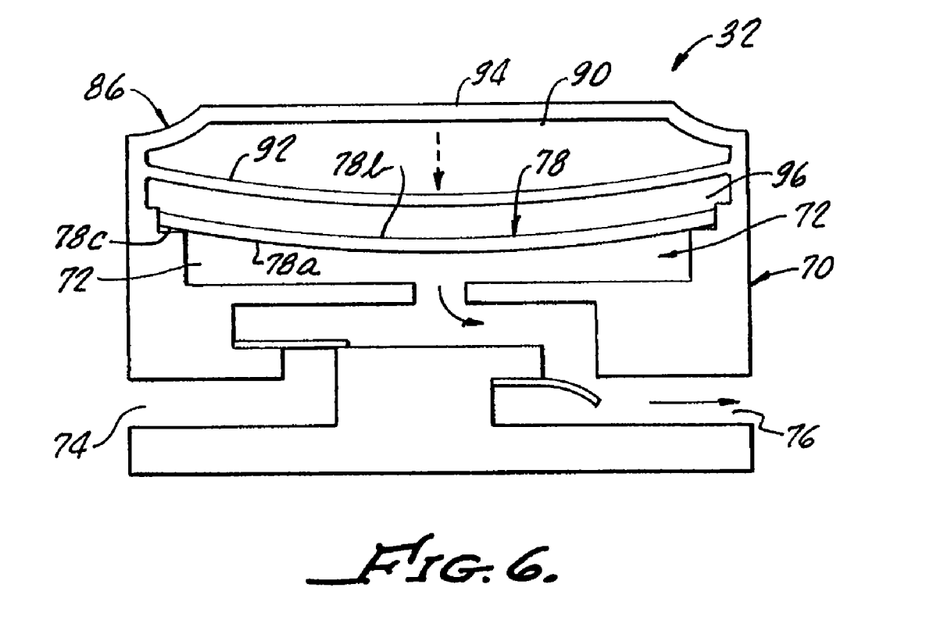
FIG. 6 is simplified cross-sectional view of a piezoelectric pump of the implantable fluid handling device in accordance with an embodiment of the invention, during expelling of fluid from the pump reservoir.

Referring now to FIGS. 5 and 6, pump device 32 comprises a body 70 at least partially defining a pump chamber 72 and having an inlet port 74 coupled to the fluid reservoir (not shown in FIGS. 5 and 6) and an outlet port 76 coupled to the inflatable portion of the gastric band (not shown in FIGS. 5 and 6). The pump 32 further comprises a piezoelectric diaphragm assembly 77 including a flexible diaphragm 78 having a working side 78a defining a surface of the pump chamber 72 and a substantially opposing actuator side 78b. The diaphragm 78 flexes in response to voltage or change in electrical potential applied to the actuator side 78b, thereby causing a change in volume of chamber 72 and effecting pumping of fluid into and out of the pump body 70, through inlet 74 and outlet 76 respectively.

The piezoelectric diaphragm assembly 77 further comprises piezoelectric elements (not shown) in functional communication with the diaphragm 78. For example, the piezoelectric elements include piezoelectric material, for example, a ceramic element and electrical contacts and connections. Because of the fragile nature of the piezoelectric elements and their connections to the diaphragm 78, the actuator side 78b of the diaphragm 78 needs to be maintained in a low relative humidity, non-condensing atmosphere in order for the pump device 32 to remain reliable and properly operable. As a result of even small changes in temperature and the relatively sealed nature of a pump in an implanted situation, liquid will tend to condense and accumulate in any void space that is not absolutely hermetic.

The diaphragm 78 of the diaphragm assembly 77 preferably comprises a metal material, for example, titanium. The diaphragm assembly 77 includes an attachment ring 78c which is preferably a biocompatible polymeric material, for example, polyphenylsulfone (PPSU).

To dramatically reduce the area available for vapor diffusion, and to provide a relatively constant gas pressure on the actuator side 78b of the diaphragm 78, the pump 32 further comprises a compressible spring assembly 86 positioned on the actuator side of the diaphragm 78. The compressible spring assembly 86 comprises a void 90 containing a gas, for example, air or other suitable gas, hermetically sealed between a first portion 92 and a substantially opposing second portion 94 which is more rigid than the first portion 92. In this exemplary embodiment, the first portion 92 comprises a thin, flexible membrane, for example a metallic membrane or foil, for example, a titanium foil. The second portion 94 may comprise the same material as the first portion 92, but is relatively more rigid than, for example, has a greater thickness relative to, the first portion 94. It is contemplated that in some embodiments of the invention, the sealed void may contain pressurized gas, for example, pressurized air. The compressible spring assembly 86 is preferably structured such that it will not adversely affect the frequency of the piezoelectric diaphragm 78.

In addition, the pump 32 further comprises a space occupying layer 96 disposed between the compressible spring assembly 86 and the actuator side 78b of the diaphragm 78. More specifically, the space occupying layer 96 comprises a hydrophobic material, for example, a hydrophobic liquid. The space occupying layer 96 preferably has a low mass such that it will not adversely affect the frequency of the piezoelectric diaphragm 78. In one embodiment of the invention, the space occupying layer 96 comprises a low durometer silicone, or a layer of silicone oil, substantially hermetically sealed between the first portion 92 of the compressible spring assembly 86 and the actuator side 78b of the diaphragm 78. The compressible spring assembly 86 may be coupled at a perimeter thereof to a surface of the pump body 70 so as to enclose the space occupying layer 96, by means of laser welding, epoxy or other suitable means.

While this invention has been described with respect to various specific examples and embodiments, it is to be understood that the invention is not limited thereto and that it can be variously practiced within the scope of the invention.

What is claimed is:

1. A system for facilitating obesity control comprising:
   a gastric banding device including an inflatable portion;
   an implantable fluid reservoir couplable to the inflatable portion;
   an implantable fluid handling device in communication with the implantable fluid reservoir and including
     a body at least partially defining a pump chamber having an inlet port coupled to the implantable fluid reservoir and an outlet port coupled to the inflatable portion,
     a piezoelectric diaphragm assembly including a working side defining a surface of the pump chamber and a substantially opposing actuator side and configured to operate at a at least one frequency,
     a compressible spring assembly positioned at the actuator side of the piezoelectric diaphragm assembly and structured to not adversely affect the at least one frequency of operation of the piezoelectric diaphragm assembly, and
     a space occupying layer disposed between the compressible spring assembly and the actuator side of the piezoelectric diaphragm assembly; and
   a drive assembly effective to cause piezoelectrical actuation of the piezoelectric diaphragm assembly thereby causing fluid to be drawn into the inlet port and out of the outlet port of the pump chamber.

2. The system of claim 1 wherein the space occupying layer comprises a hydrophobic material.

3. The system of claim 1 wherein the space occupying layer comprises a hydrophobic liquid.

4. The system of claim 1 wherein the space occupying layer comprises silicone oil.

5. The system of claim 1 wherein the space occupying layer is substantially hermetically sealed between the compressible spring assembly and the actuator side of the piezoelectric diaphragm assembly.

6. The system of claim 1 wherein the compressible spring assembly comprises a sealed void.

7. The system of claim 6 wherein the sealed void contains a gas.

8. The system of claim 6 wherein the sealed void contains air.

9. The system of claim 6 wherein the sealed void contains a pressurized gas.

10. The system of claim 1 wherein the compressible spring assembly comprises a hermetically sealed void.

11. The system of claim 1 wherein the compressible spring assembly comprises a first portion and a substantially opposing second portion which is structured to be more rigid than the first portion.

12. The system of claim 11 wherein the compressible spring assembly comprises a sealed void defined between the first portion and the second portion.

13. The system of claim 11 wherein the first portion comprises a membrane.

14. The system of claim 11 wherein the first portion comprises a metallic membrane.

15. The system of claim 11 wherein the first portion comprises a titanium membrane.

16. The system of claim 11 wherein the first portion and the second portion both comprise the same material.

17. The system of claim 11 wherein the first portion and the second portion both comprise titanium.

18. An implantable fluid handling device for use with a gastric banding device having an inflatable portion for forming a stoma, the device comprising:
   a piezoelectric pump assembly comprising
     a body at least partially defining a pump chamber having an inlet port couplable to a fluid reservoir and an outlet port couplable to an inflatable portion of a gastric banding device,
     a piezoelectric diaphragm assembly including a working side, defining a surface of the pump chamber and a substantially opposing actuator side and configured to operate at a at least one frequency,
     a compressible spring assembly positioned at the actuator side of the piezoelectric diaphragm assembly and structured to not adversely affect the at least one frequency of operation of the piezoelectric diaphragm assembly, and
     a space occupying layer disposed between the compressible spring assembly and the actuator side of the piezoelectric diaphragm assembly; and
   a drive assembly effective to actuate the piezoelectric pump assembly.

* * * * *